United States Patent
Chang et al.

(10) Patent No.: US 8,414,938 B2
(45) Date of Patent: Apr. 9, 2013

(54) SCHISANDRAE FRUCTUS EXTRACTS FOR INHIBITION OR PREVENTION OF H1N1 INFLUENZA VIRUS INFECTION AND ITS APPLICATION THEREOF

(75) Inventors: Wen-Liang Chang, Taipei (TW); Chen-Wen Yao, Taipei (TW); Chi-Hong Chu, Taipei (TW); An-Rong Lee, Taipei (TW); Ann Chen, Taipei (TW); Wen-Hsin Huang, Taipei (TW); Kuo-Yuan Hwa, Taipei (TW); Chiao-Ying Chien, Taipei (TW); Chien-Yi Pai, Taipei (TW)

(73) Assignee: National Defense Medical Center, Taipei (TW)

( * ) Notice: Subject to any disclaimer, the term of this patent is extended or adjusted under 35 U.S.C. 154(b) by 0 days.

(21) Appl. No.: 13/298,607

(22) Filed: Nov. 17, 2011

(65) Prior Publication Data
US 2012/0189719 A1 Jul. 26, 2012

(30) Foreign Application Priority Data
Jan. 24, 2011 (TW) .............................. 100102500 A

(51) Int. Cl.
*A01N 65/00* (2009.01)
(52) U.S. Cl.
USPC .......................................................... 424/725
(58) Field of Classification Search .................. None
See application file for complete search history.

(56) References Cited

U.S. PATENT DOCUMENTS
2009/0280200 A1 * 11/2009 Pan et al. ...................... 424/757

* cited by examiner

*Primary Examiner* — Michael Meller
(74) *Attorney, Agent, or Firm* — WPAT, P.C.; Anthony King

(57) ABSTRACT

Disclosed are an Schisandrae fructus extract for inhibition or prevention of influenza and its application, wherein the Schisandrae fructus extract is obtained by water, methanol, or ethanol extraction process and the extract comprises compounds such as schisandrone, benzoylgomisin P, wulignan A1, epigomisin O, epiwulignan A1, and tigloylgomisin P. The extracts and purified compounds of Schisandrae fructus has anti-influenza virus H1N1 and H1N1-TR (a Tamiflu drug resistant virus strain) activities, therefore the extracts and the purified compounds of Schisandrae fructus can be applied as an inhitibory agent of a pharmaceutical composition for treatment or prevention agent for influenza infection.

1 Claim, No Drawings

SCHISANDRAE FRUCTUS EXTRACTS FOR INHIBITION OR PREVENTION OF H1N1 INFLUENZA VIRUS INFECTION AND ITS APPLICATION THEREOF

BACKGROUND OF THE INVENTION

1. Field of the Invention

The present invention relates to a herbal extract having anti-influenza virus activity, especially relates to a Schisandrae fructus extract for inhibition or prevention of influenza and its application.

2. The Prior Arts

Every year influenza virus causes epidemic of acute respiratory diseases around the world and has become one of the most life threatening pandemic virus. Influenza virus belongs to the family of Orthomyxoviridae and is classified into type A, B, and C on the basis of its antigen of nucleuoprotein, of which influenza virus B and C mainly infect human and variance of these two types of virus mutants is less significant. However, influenza virus A widely infects birds and mammals such as human, pig and horse. Furthermore, antigen of influenza virus A displays a significant variety and new sub-type mutants are evolved frequently so that new mutants may be able to infect a new host. It has been recorded that a few previous global pandemics are caused by influenza virus A, indicating that influenza virus A can cause serious damage to human health among immuno-deficiency patients, and sometimes jeopardizes human life. Currently treatments of seasonal influenza symptoms are mainly supportive cares, and these therapeutics can be divided into four types. The first type of therapeutics is vaccine, the most common practice of preventive method. However, this approach can't produce protective effect against new evolving virus types. The second type of therapeutics is M2 protein inhibitors such as amantadine and rimantadine, in which replication of influenza virus A is inhibited by blocking M2 ion channel to release RNA. However, this group of therapeutics is ineffective against influenza virus B and it causes neurological and psychological side effects as well as causes drug resistance. The third type of therapeutics is neuraminidase inhibitors such as oseltamivir, zanamivir, and peramivir. Neuraminidase is involved in the release of progeny virus from infected cells, by cleaving sugars that bind the mature viral particles. Specifically, neuraminidase cleaves the α-ketosidic bond that links a terminal neuraminic acid residue to the adjacent oligosaccharide moiety, neuraminidase is therefore essential for the movement of the virus to and from sites of infection in the respiratory tract. Zanamivir and oseltamivir inhibit viral neuraminidase, which plays an important role in viral proliferation and is stably present in both influenza viruses A and B, and both agents have been used for the treatment and prophylaxis of influenza viruses A and B. However, zanamivir is an inhaled form and its acceptability is low. Oseltamivi is widely accepted but statistics of WHO study have shown an emerging concern of drug resistance. The forth method is treatment with virus replication inhibitors such as ribavirin, viramidine and T-705. These drugs can block synthetic pathways of virus proteins. Although the above mentioned treatments are used clinically, there are many disadvantages and side effects and virus mutants are continuingly evolving. Therefore, it is important and necessary to develop new drugs for treatment or prevention of influenza virus.

The dried fruits of *Schisandra chinensis* (Turca) Baill or *Schisandra sphenanthera* Rehd. et Wils (family of Schisandraceae), named of Wuweizi or Schisandrae fructus in Chinese traditional medicine, are used as an antitussive, tonic, and sedative agent in China and Taiwan. According to the traditional Chinese medicine, characteristics of Schisandrae fructus are mild, with sour and salty taste, and belonging to the lung, kidney, and heart channel tropism. Functions that provided by Schisandrae fructus include astringent action to the lung, nourishment to the kidney, increase of body strength, stopping sweating, and calm of mind. Furthermore, pharmaceutical studies have found that crude extracts of Schisandrae fructus has functions of calmness, hypnotism, protection of neuron cells and liver, anti-oxidation, anti-cancer, lowering blood sugar, enhancement of bone cell growth, and anti-hepatitis B virus activity. Currently chemical constituents found in Schisandrae fructus include lignans, volatile oils, glycosides, organic acids, fatty acids, vitamin C, and vitamin E are isolated, wherein studies of lignans have shown that this ingredient has biological activity of anti-Alzheimer's disease, liver protection, anti-inflammation, anti-oxidation, as well as anti-HIV virus.

Mutants of influenza virus vary significantly and spread rapidly. When a new virulent mutant of influenza virus emerges and causes new type of flu epidemic, this new epidemic may rapidly distribute across borders around the world. Human life will be greatly threatened and global social and economic activities will be impacted. Thus there is a great need to develop effective anti-influenza virus drugs.

SUMMARY OF THE INVENTION

To inhibit influenza virus and to treat flu effectively, the present invention provides an isolated Schisandrae fructus extract for inhibiting or preventing of influenza virus H1N1 and H1N1-TR (a Tamiflu drug resistant virus strain), and a method for treating or preventing influenza, wherein the extract is obtained by water or alcoholic solvent extraction such as methanol or ethanol. The methanol/ethanol extract of Schisandrae fructus is further treated with a solvent selected from the group consisting of n-hexane, dichloromethane, ethyl acetate and n-butnaol. The Schisandrae fructus extract of the present invention comprises a compound or a mixture thereof with the following structural formula I, II, III, IV, V, VI.

(III)

(IV)

(V)

(VI)

The present invention further provides a composition and a method for treating or preventing influenza, wherein composition comprises an effective amount of the compound of structural formula I, II, III, IV, V, VI or a mixture thereof and a pharmaceutically acceptable carrier.

The compounds of structural formula I, II, III, IV, V, VI contained in an isolated Schisandrae fructus extract or the composition are derived from the methanol extract of Schisandrae fructus further treated with dichloromethane, and subsequently isolated and purified by silica gel column chromatography, low pressure reverse phase chromatography or high pressure column chromatography. The Schisandrae fructus extract can inhibit the activity of influenza virus H1N1 already existing in the infected cells. Furthermore, the activity of influenza virus H1N1 is immediately inhibited when the composition co-exists with influenza virus H1N1 to treat influenza. In addition, the normal cells treated with the Schisandrae fructus extract of the present invention and then followed by challenging with H1N1 virus can be protected from influenza virus H1N1 infection and consequently preventive from infection of the H1N1 flu.

The present invention is further explained in the following embodiment illustration and examples. Those examples below should not, however, be considered to limit the scope of the invention, it is contemplated that modifications will readily occur to those skilled in the art, which modifications will be within the spirit of the invention and the scope of the appended claims.

DETAILED DESCRIPTION OF THE PREFERRED EMBODIMENT

In one embodiment, the dried fruits of *Schisandra chinensis*, Schisandrae fructus, were first extracted with alcoholic solvent such as methanol, and then were treated with different polarity solvents such as dichloromethane, ethyl acetate, or n-butanol to obtain the crude extracts of Schisandrae fructus. These crude extracts were tested and screened for their anti-viral activity, and the results showed that extract derived from dichloromethane extraction had better anti-influenza virus activity. The dichloromethane extract of Schisandrae fructus was further subjected to purification using silica gel column chromatography and analyzed for its anti-flu activity. Several compounds with good anti-influenza virus activity were obtained, and these extracts and purified compounds of Schisandrae fructus could be applied clinically for treatment or prevention of flu.

EXAMPLE 1

(1) Preparation of Schisandrae fructus Extract—Methanol Extraction

Schisandrae fructus was grounded into powder. 11.5 kg of the Schisandrae fructus powder was extracted with methanol six times at room temperature. Then the combined extract was concentrated under reduced pressure using rotary concentrator and 3.2 kg of methanol crude extract (designated as SCCH-M) was obtained. In addition, the purpose of grinding of Schisandrae fructus into fine powder was to facilitate extraction process. Therefore, any physical method, such as maceration or cutting, that could cut the dry fruit into small particles might be used but the present invention was not limited thereof.

The methanol crude extract (SCCH-M) was dissolved in 90% methanol, followed by partition extraction four times by n-hexane at a volume ratio of 1:1 and thus obtained 529.0 g of n-hexane crude extract (designated as SCCH-H). Then the water phase of n-hexane crude extract was extracted in proper order with equal volume of dichloromethane, ethyl acetate and n-butanol. 78.9 g of dichloromethane crude extract (designated as SCCH-D), 102.6 g of ethyl acetate crude extract (designated as SCCH-E), 458.0 g of n-hexane crude extract (designated as SCCH-B) and 2419.5 g of water crude extract (designated as SCCH-W) were collected.

(2) Preparation of Schisandrae Fructus Extract—Ethanol Extraction or Water Extraction Schisandrae fructus was grinded into powder with grinder. 100 g of the Schisandrae fructus powder was extracted with 6 to 10 fold volume of 95% ethanol at room temperature twice, and the combined extract was concentrated under reduced pressure by concentrator thus 40 g of ethanol crude extract (designated as SCCH-EtOH) was collected. Schisandrae fructus were grinded into powder with grinder. 100 g of the powder was extracted with hot water twice followed by concentration at reduced pressure. 35 g of water crude extract was obtained (designated as SCCH-H$_2$O). In addition, the purpose of grinding of Schisandrae fructus into fine powder was to facilitate extraction process. Therefore, any physical method, such as maceration or cutting, that could cut the dry fruit into small particles might be used but the present invention was not limited thereof.

The ethanol crude extract (SCCH-EtOH) and the water crude extract (SCCH-H$_2$O) was subjected to further extraction using solvents including n-hexane, dichloromethane, ethyl acetate or n-butanol, according to the methanol extraction process as mentioned above.

EXAMPLE 2

Analysis of Anti-Influenza Virus Activity of Schisandrae fructus Extracts

The present invention was further exemplified with in vitro MTT screening method to analyze anti-influenza virus activity of Schisandrae fructus extracts. In addition, minimum inhibitory concentration (MIC) method was used to study pharmacotoxicity of Schisandrae fructus extracts. Based on these results, extracts with preferred antiviral activity was screened.

Cell line was cultivated and infected with influenza virus. Cell line used in the embodiment of the present invention was Madin-Darby canine kidney cells (MDCK cell (BCRC 60004), purchased from BCRC). Cells was cultivated in Dulbeco's modified Eagle's medium (DMEM) supplemented with 10% fetal bovine serum (FBS) in 96-well plate (2×10$^4$ cells/well) and incubated at 37° C. in an incubator containing controlled CO$_2$ level (5%) for 20~24 hrs. After incubation, cells were washed with 110 µl of PBS twice. Then in each well 100 µl of tosylsulfonyl phenylalanyl chloromethyl ketone-treated trypsin (TPCK) medium was added and placed in incubator.

The extracts, including SCCH-M, SCCH-H, SCCH-D, SCCH-E, SCCH-B and SCCH-W, prepared according to Examples 1 were first dissolved in DMSO at a concentration of 200 mg/ml. Then SCCH-M was diluted with TPCK medium to 100 µg/ml and 300 µg/ml solutions, respectively. The rest of the crude extract solutions were also diluted with TPCK medium to 50 µg/ml and 100 µg/ml, respectively, and the solutions were ready for further tests.

Then, The SCCH-M was applied according to the following seven test conditions: (1) Cultivated MDCK cells were collected after removal of TPCK medium then infected with 50 µl of influenza virus H1N1 at 0.01 MOI (multiplicity of infection) for one hour. After infection, 50 µl of SCCH-M was added. This group was designated as V1+D group; (2) MDCK cells, harvested after removal of TPCK medium, were first treated with 50 µl SCCH-M for one hour. Then, cells were infected with 50 µl of influenza virus H1N1 at 0.01 MOI. This group was designated as D1+V group; (3) MDCK cells, collected after removal of TPCK medium, were treated with 50 µl SCCH-M and infected with 50 µl influenza virus H1N1 at 0.01 MOI at the same time. This group was designated as D+V group; (4) MDCK cells, harvested after removal of TPCK medium, were added with 50 µl SCCH-M and 50 µl TPCK medium. This group was designated as D group; (5) MDCK cells, harvested after removal of TPCK medium, were infected with 50 µl influenza virus H1N1 at 0.01 MOI and added with 50 µl of TPCK medium. This group was designated as V group; (6) MDCK cells, harvested after removal of TPCK medium, were added with 100 µl TPCK medium. This group was designated as control group Mock; and (7) The blank group contained neither MDCK cells nor TPCK medium.

On the other hand, the extracts of Schisandrae fructus, including SCCH-H, SCCH-D, SCCH-B and SCCH-W, were used in the following five tests: (1) MDCK cells, harvested after removal of TPCK medium, were added with 50 µl of above mentioned crude extracts respectively and infected with 50 µl influenza virus H1N1 at 0.01 MOI at the same time. This group was designated as D+V group. (2) MDCK cells, collected after removal of TPCK medium, were treated with 50 µl of Schisandrae fructus extract and 50 µl of TPCK medium. This group was designated as D group. (3) MDCK cells, harvested after removal of TPCK medium, were infected with 50 µl influenza virus H1N1 at 0.01 MOI and added with 50 µl of TPCK medium. This group was designated as V group. (4) MDCK cells, harvested after removal of TPCK medium, were added with 100 µl of TPCK medium. This group was designated as control group Mock; and (5) the blank group contained neither MDCK cells nor TPCK medium.

These test groups were incubated in an incubator with controlled level of 5% CO$_2$ at 37° C. for 48 hrs. When the V group (the group treated with influenza virus alone) showed ≧75% of cell apoptosis under the microscope, MTT analysis was performed immediately. In the MTT test, the D1+V group, V1+D group, D+V group, D group, V group, and the Mock control group were supplemented with 20 µl of MTT agent (3-[4,5-dimethylthiazol-2-yl]2,5-diphenyltetrazolium bromide) reagent (concentration at 5 mg/ml) and then allowed to react for 5 hours. In another set of test, the D1+V group, V1+D group, D+V group, D group, V group, and the Mock control group were supplemented with 25 µl of glycine buffer and 100 µl of DMSO, followed by enzyme immunoanalysis (BIOTEK CERES 900 EIA Reader) at 540 nm Cell survival ratio was calculated according to the following formulation:

$$\text{Cell survival ratio} = \frac{(D1+V/V1+D/D+V/D/V) - \text{Blank}}{\text{Mock}} \times 100\%$$

For cell survival ratio ≦25%, >25% but ≦50%, >50% but ≦75%, >75% but ≦100%, or >100%, the results were recorded as +/−, +, ++, +++, or ++++, respectively. In which, the extracts that indicating effectiveness was defined as when (1) the cell survival ratio of the V group (the group that was treated with virus alone) must be less than 50% and (2) the extracts that could reverse cell apoptosis resulting from virus infection and the cell survival ratio must be higher than +++. The results were shown in Tables 1 and 2.

In addition, serial dilution of crude extract of SCCH-M was prepared (100, 75, 50, 25, 12.5, and 6.25 µg/ml respectively), and its minimal inhibition concentration (MIC) of anti-influenza virus activity was determined according to the methods described above.

TABLE 1

Anti-influenza virus activity of methanol extract of Schisandrae fructus

|  | 300 µg/ml | | 100 µg/ml | |
| --- | --- | --- | --- | --- |
|  | V1 + D | D | V1 + D | D |
| SCCH-M | ++++ | ++++ | ++++ | ++++ |

Referring to Table 1, when cells infected with influenza virus H1N1 for 1 hour then treated with 100 µg/ml or 300 µg/ml of SCCH-M, the cell survival ratio could reach 100%, suggesting that SCCH-M could effectively inhibit the activity of influenza virus H1N1 that already existing in the infected cells. On the other hand, when cells were treated with SCCH-M for 1 hour first and followed by infection with H1N1 influenza virus, it could be found that cells were protected from influenza virus H1N1 infection. Thus, the results indicated that extract of Schisandrae fructus could be applied to protect cells from H1N1 influenza virus infection. Furthermore, the minimal inhibition concentration (MIC) of the V1+D group, influenza virus H1N1 infection for 1 hour first then supplemented with SCCH-M, was 50 µg/ml; and the MIC of D1+V group, cells treated with SCCH-M for 1 hour first then H1N1 influenza virus infection, was 25 µg/ml; and the MIC of D+V group, cells treated with SCCH-M and H1N1 infection simultaneously, was 3.125 µg/ml. The present invention also found that SCCH-EtOH and SCCH-$H_2O$ could effectively inhibit the activity of influenza virus H1N1 in the infected cells (referring to Table 11).

TABLE 2

Anti-influenza virus activity of various extracts derived from partition extraction of SCCH-M

|  | 100 µg/ml | | 50 µg/ml | |
| --- | --- | --- | --- | --- |
|  | D + V | D | D + V | D |
| SCCH-H | +/− | +/− | +/− | ++++ |
| SCCH-D | ++++ | +++ | + | +++ |
| SCCH-E | +/− | +++ | +/− | +++ |
| SCCH-B | +/− | +++ | +/− | +++ |
| SCCH-W | +/− | +++ | +/− | +++ |

The above described methanol extract, ethanol extract or water extract of Schisandrae fructus that showed anti-influenza virus activity were further extracted with other solvents. The results showed that among a n-hexane extract, a dichloromethane extract, a ethyl acetate extract, a n-butanol extract, and water extract of Schisandrae fructus, the dichloromethane extract at concentration of 100 µg/ml had highest anti-viral activity comparing to other extracts. Furthermore, the cell survival ratio was larger than 100% in the dichloromethane extract treated sample. The phenomena indicated that the dichloromethane extract could inhibit cell apoptosis resulting from influenza virus H1N1 infection, and consequently leading to survival of cells.

EXAMPLE 3

Preparation and Isolation of Compounds in a Schisandrae fructus Extract

To further confirm the active ingredient of anti-viral activity of Schisandrae fructus, the present invention used 78.9 g of SCCH-D extract to perform silica column chromatography (70-230 mesh). The elution was performed using $CH_2Cl_2$:$CH_3OH$ (ratio 9:1) as mobile phase with gradually increasing in polarity by increasing amount of MeOH. Eight fractions, including 18.2 g of SCCH-D1, 12.8 g of SCCH-D2, 2.2 g of SCCH-D3, 18.8 g of SCCH-D4, 5.1 g of SCCH-D5, 0.4 g of SCCH-D6, 17.9 g of SCCH-D7 and 7.5 g of SCCH-D8 respectively, were collected and tested their anti-viral activities. The results showed that SCCH-D2, SCCH-D3 and SCCH-D4 at concentrations of 100 µg/ml and 50 µg/ml both had anti-viral activity. SCCH-D1 at concentration of 50 µg/ml showed effectiveness, while SCCH-D6 showed anti-viral activity at concentration of 100 µg/ml.

Next, SCCH-D1 that showed better anti-viral activity was separated with reverse phase chromatography (Lobar RP-8), using 80% MeOH/$H_2O$ as mobile phase. Eight fractions, including 2.1 g of SCCH-D11, 0.9 g of SCCH-D12, 1.7 g of SCCH-D13, 2.0 g of SCCH-D14, 1.4 g of SCCH-D15, 0.7 g of SCCH-D16, 3.4 g of SCCH-D17, and 4.0 g of SCCH-D18 were collected.

Among which, SCCH-D12 was purified again using preparative HPLC (prep. HPLC, C-18) chromatography and 60~65% of MeOH/$H_2O$ as mobile phase, at flow rate 7 ml/min. Wavelength of UV detector was set at 254 nm After elution, 29 mg of wulignan A1 and 20 mg of epiwulignan A1 were collected.

On the other hand, SCCH-D13 was purified again using preparative HPLC (prep. HPLC, C-18) chromatography and 78% of $CH_3CN/H_2O$ as mobile phase, at flow rate 7 ml/min Wavelength of UV detector was set at 254 nm In total, nine fractions, including 94 mg of SCCH-D131, 544 mg of SCCH-D132, 413 mg of SCCH-D133, 296 mg of SCCH-D134, 21 mg of SCCH-D135, 5 mg of SCCH-D136, 5 mg of SCCH-D137, 12 mg of SCCH-D138 and 277 mg of SCCH-D139, were collected. Among which, SCCH-D132 was purified again using preparative HPLC (prep. HPLC, C-18) chromatography and 65% of MeOH/$H_2O$ as mobile phase, at flow rate 7 ml/min Wavelength of UV detector was set at 254 nm 37 mg of schisandrone was collected. SCCH-D133 was first purified using preparative HPLC (prep. HPLC, C-18) chromatography and 70% of MeOH/$H_2O$ as mobile phase, at flow rate 7 ml/min Wavelength of UV detector was set at 254 nm Then the collected fractions were subjected to prep. TLC, $SiO_2$ gel chromatography, using $CH_2Cl_2$:MeOH=9:1 for chromatography development. Then 9 mg of epigomisin 0 was collected. SCCH-D134 was purified using prep. HPLC, C-18 column and 58% of $CH_3CN/H_2O$ as mobile phase, at flow rate 7 ml/min Wavelength of UV detector was set at 254 nm. Then 23 mg of benzoylgomisin P and 67 mg of tigloylgomisin P were collected.

In addition, dichloromethane layers of the ethanol extract and the water extract of Schisandrae fructus were analyzed according to the processes described above. The results also demonstrated that compounds of formula I, II, III, IV, V, or VI were found in the extract.

The structure of these purified compounds were analyzed and identified.

(1) Schisandrone was the compound of formula I, colorless needle crystal, melting point 176-177° C. Schisandrone had molecular peak of EI-MS at [M]$^+$m/z: 356 and its molecular formulation was $C_{21}H_{24}O_5$. Maximum wavelength of UV absorption were at 235 (4.62), 254 (3.73, sh), 277 (4.36), 317 (4.04) nm. The results of NMR analysis value was shown in Table 3.

TABLE 3

(I)

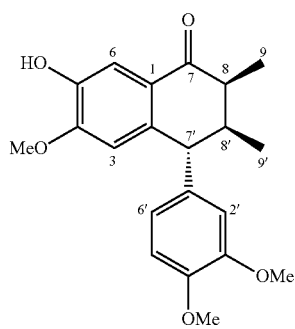

The results of NMR spectrum analysis of schisandrone

| Position | (CDCl$_3$, 125 MHz) δ C mult. | (CDCl$_3$, 500 MHz) δ H mult. (J in Hz) |
|---|---|---|
| 1 | 126.8 s | |
| 2 | 137.8 s | |
| 3 | 111.3 d | 6.40 s |
| 4 | 151.3 s | |
| 5 | 144.7 s | |
| 6 | 111.9 d | 7.59 s |
| 7 | 199.9 s | |
| 8 | 42.45 d | 2.74 m |
| 9 | 11.9 q | 1.09 d (7.0) |
| 1' | 136.4 s | |
| 2' | 111.8 d | 6.52 d (1.7) |
| 3' | 149.0 s | |
| 4' | 147.7 s | |
| 5' | 110.9 d | 6.75 d (8.2) |
| 6' | 121.0 d | 6.59 dd (1.7, 8.2) |
| 7' | 50.4 d | 3.94 d (5.3) |
| 8' | 42.6 d | 2.39 m |
| 9' | 15.9 q | 0.96 d (7.0) |
| C4-OMe | 56.0 q | 3.77 s |
| C3'-OMe | 55.8 q | 3.79 s |
| C4'-OMe | 55.9 q | 3.84 s |
| OH | | 5.66 br |

(2) Benzoylgomisin P was the compound of formula II, white powder, melting point 113-115° C. Benzoylgomisin P had molecular peak of EI-MS at [M+Na]$^+$m/z: 559. Maximum wavelength of UV absorption were at 225 (4.59), 250 (3.94, sh), 276 (3.60, sh) nm. The molecular formula was $C_{30}H_{32}O_9$. The results of NMR analysis value was shown in Table 4.

TABLE 4

(II)

The results of NMR spectrum analysis of Benzoylgomisin P

| Position | (CDCl$_3$, 125 MHz) δ C mult. | (CDCl$_3$, 500 MHz) δ H mult. (J in Hz) |
|---|---|---|
| 1 | 151.1 s | |
| 2 | 141.1 s | |
| 3 | 152.4 s | |
| 4 | 106.1 d | 6.95 s |
| 5 | 133.2 s | |
| 6 | 78.3 d | 5.79 s/β |
| 7 | 75.2 s | |
| 8 | 46.6 d | 1.94 m |
| | | 2.09 dd (13.5, 9.9)/α |
| 9 | 36.7 t | 2.19 dd (13.9, 1.0)/β |
| 10 | 136.7 s | |
| 11 | 103.1 d | 6.50 s |
| 12 | 149.5 s | |
| 13 | 135.7 s | |
| 14 | 141.6 s | |
| 15 | 123.0 s | |
| 16 | 119.5 s | |
| 17 | 18.8 q | 1.11 d (7.1) |
| 18 | 17.6 q | 1.19 s |
| OMe | 56.0 q | 3.60 s |
| | 60.0 q | 3.83 s |
| | 60.6 q | 3.83 s |
| | 60.9 q | 3.88 s |
| —OCH$_2$O— | 101.0 t | 5.97 s |
| Benzoyl | | |
| 1' | 130.3 s | |
| 2', 6' | 129.5 d | 8.02 |
| 3', 5' | 128.5 d | 7.43 |
| 4' | 132.8 d | 7.55 |
| C=O | 165.2 s | |
| OH | | 5.66 br |

(3) Wulignan A1 was the compound of formula III, white powder, melting point 123-125° C. Wulignan A1 had molecular peak of HREI-MS at [M]$^+$m/z: 342.1464. The molecular formula was $C_{20}H_{22}O_5$. Maximum wavelength of UV absorption were at 235 (4.86), 254 (4.07, sh), 278 (4.61), 318 (2.28) nm. The results of NMR analysis value was shown in Table 5.

TABLE 5

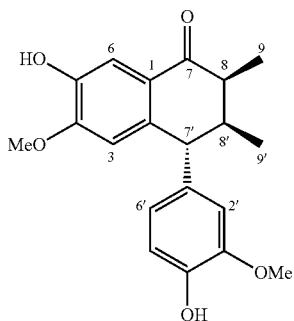 [SMILES: COc1cc([C@@H]2c3cc(OC)c(O)cc3C(=O)[C@@H](C)[C@H]2C)ccc1O]

(III)

The results of NMR spectrum analysis of wulignan A1

| Position | δ C mult. | δ H mult. (J in Hz) |
|---|---|---|
| 1 | 126.3 s | |
| 2 | 137.9 s | |
| 3 | 111.3 d | 6.40 s |
| 4 | 151.3 s | |
| 5 | 144.7 s | |
| 6 | 111.9 d | 7.59 s |
| 7 | 200.0 s | |
| 8 | 42.6 d | 2.74 m |
| 9 | 11.9 q | 1.09 d (7.0) |
| 1' | 135.8 s | |
| 2' | 111.0 d | 6.53 d (1.6) |
| 3' | 146.2 s | |
| 4' | 144.3 s | |
| 5' | 114.2 d | 6.81 d (8.6) |
| 6' | 121.8 d | 6.51 dd (1.6, 8.6) |
| 7' | 50.5 d | 3.93 d (5.3) |
| 8' | 42.6 d | 2.36 m |
| 9' | 15.9 q | 0.96 d (7.0) |
| C4-OMe | 55.9 q | 3.77 s |
| C3'-OMe | 56.0 q | 3.78 s |
| OH | | 5.57 brs |
| OH | | 5.67 brs |

(4) Epigomisin O was the compound of formula IV, white powder, melting point 80-81° C. Epigomisin O had molecular peak of EI-MS at [M]⁺m/z: 416. The molecular formula was $C_{23}H_{28}O_7$. Maximum wavelength of UV absorption were at 221 (4.62), 255 (4.02, sh), 275 (3.75, sh) nm. The results of NMR analysis value was shown in Table 6.

TABLE 6

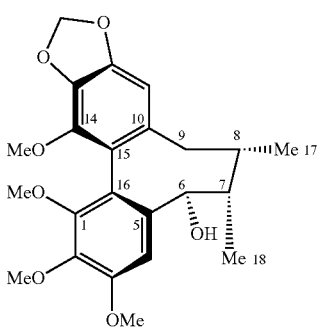

(IV)

The Results of NMR spectrum analysis of epigomisin O

| Position | (CDCl₃, 125 MHz) δ C mult. | (CDCl₃, 500 MHz) δ H mult. (J in Hz) |
|---|---|---|
| 1 | 151.1 s | |
| 2 | 140.6 s | |

TABLE 6-continued

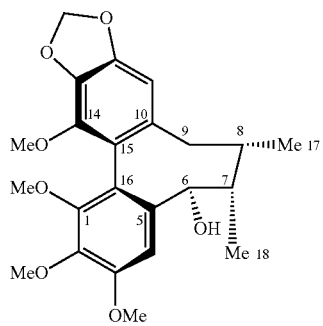

(IV)

The Results of NMR spectrum analysis of epigomisin O

| Position | (CDCl₃, 125 MHz) δ C mult. | (CDCl₃, 500 MHz) δ H mult. (J in Hz) |
|---|---|---|
| 3 | 152.2 s | |
| 4 | 106.2 d | 6.99 s |
| 5 | 136.4 s | |
| 6 | 73.4 d | 4.55 d (1.4)/β |
| 7 | 42.5 d | 1.99 m |
| 8 | 39.2 d | 1.89 m |
| | | 1.97 dd (13.5, 1.9)/α |
| 9 | 34.66 t | 2.09 dd (13.4, 9.4)/β |
| 10 | 137.9 s | |
| 11 | 102.8 d | 6.42 s |
| 12 | 149.1 s | |
| 13 | 134.5 s | |
| 14 | 140.8 s | |
| 15 | 119.5 s | |
| 16 | 121.1 s | |
| 17 | 22.0 q | 0.98 d (7.2) |
| 18 | 7.7 q | 0.68 d (7.1) |
| 1-OMe | 60.6 q | 3.89 s |
| 2-OMe | 59.6 q | 3.83 s |
| 3-OMe | 55.9 q | 3.52 s |
| 14-OMe | 61.0 q | 3.89 s |
| —OCH₂O— | 100.8 t | 5.92 s |

(5) Epiwulignan A1 was the compound of formula V, light yellow crystal, melting point 154-156° C. Epiwulignan A1 had molecular peak of EI-MS at [M]⁺m/z: 342.1462. The molecular formula was $C_{20}H_{22}O_5$. Maximum wavelength of UV absorption were at 231 (4.73), 255 (4.24, sh), 275 (4.39), 313 (4.00) nm. The results of NMR analysis value was shown in Table 7.

TABLE 7

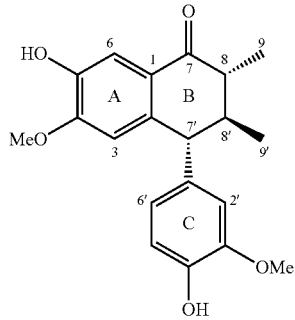

(V)

The results of NMR spectrum analysis of epiwulignan A1

| Position | δ C mult. | δ H mult. (J in Hz) |
|---|---|---|
| 1 | 126.4 s | |
| 2 | 140.8 s | |
| 3 | 110.6 d | 6.15 s |

TABLE 7-continued

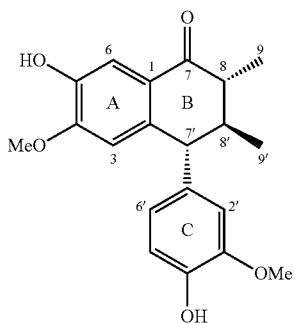

(V)

The results of NMR spectrum analysis of epiwulignan A1

| Position | δ C mult. | δ H mult. (J in Hz) |
|---|---|---|
| 4 | 150.8 s | |
| 5 | 144.4 s | |
| 6 | 111.7 d | 7.56 s |
| 7 | 198.8 s | |
| 8 | 48.6 d | 2.35 m |
| 9 | 12.5 q | 1.28 d (6.7) |
| 1' | 135.8 s | |
| 2' | 110.9 d | 6.52 d (1.2) |
| 3' | 146.9 s | |
| 4' | 144.4 s | |
| 5' | 114.2 d | 6.89 d (8.0) |
| 6' | 122.9 d | 6.69 dd (1.2, 8) |
| 7' | 53.5 d | 3.63 d |
| 8' | 43.8 d | 2.04 m |
| 9' | 17.9 q | 0.90 d (6.5) |
| C4-OMe | 55.9 q | 3.63 s |
| C3'-OMe | 56.0 q | 3.80 s |
| OH | | 5.55 brs |
| | | 5.58 brs |

(6) Tigloylgomisin P was the compound of formula VI, white powder, melting point 114-115° C. Tigloylgomisin P had molecular peak of EI-MS at [M+Na]+/m/z: 537. The molecular formula was $C_{28}H_{34}O_9$. Maximum wavelength of UV absorption were at 222 (4.55), 256 (3.81, sh), 275 (3.54, sh) nm The results of NMR analysis value was shown in Table 8.

TABLE 8

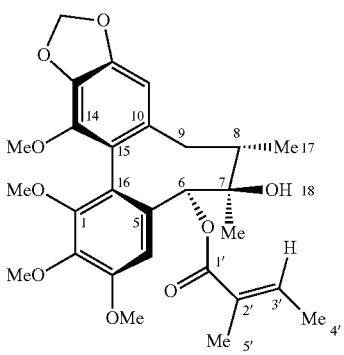

(VI)

The Results of NMR spectrum analysis of tigloylgomisin P

| Position | (CDCl₃, 125 MHz) δ C mult. | (CDCl₃, 500 MHz) δ H mult. (J in Hz) |
|---|---|---|
| 1 | 151.0 s | |
| 2 | 141.4 s | |
| 3 | 152.3 s | |

TABLE 8-continued

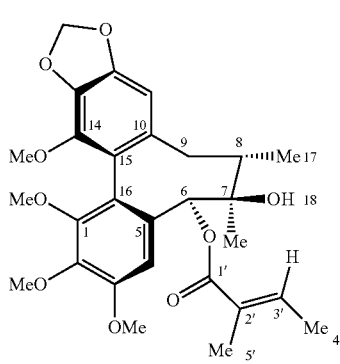

(VI)

The Results of NMR spectrum analysis of tigloylgomisin P

| Position | (CDCl₃, 125 MHz) δ C mult. | (CDCl₃, 500 MHz) δ H mult. (J in Hz) |
|---|---|---|
| 4 | 106.1 d | 6.87 s |
| 5 | 133.0 s | |
| 6 | 77.6 d | 5.50 s/β |
| 7 | 75.8 s | |
| 8 | 46.5 d | 1.88 m |
| 9 | 36.6 t | 2.10 m |
| 10 | 136.6 s | |
| 11 | 103.0 d | 6.47 s |
| 12 | 149.4 s | |
| 13 | 135.5 s | |
| 14 | 141.0 s | |
| 15 | 119.5 s | |
| 16 | 122.8 s | |
| 17 | 17.5 q | 1.06 d (8.0) |
| 18 | 18.8 q | 1.08 s |
| 1-OMe | 60.6 q | 3.58 s |
| 2-OMe | 60.9 q | 3.88 s |
| 3-OMe | 55.9 q | 3.85 s |
| 14-OMe | 59.9 q | 3.79 s |
| | | 5.93 d (5.3) |
| —OCH₂O— | 101.1 s | 5.94 d (5.3) |
| 2' | 128.8 s | |
| 3' | 137.5 d | 6.89 m |
| 4' | 14.4 q | 1.78 d (1.8) |
| 5' | 12.2 q | 1.83 s |
| C=O | 166.6 s | |

EXAMPLE 4

Anti-Viral Activity Analysis of Purified Compounds of Schisandrae fructus Extracts Schisandrone, benzoylgomisin P, wulignan A1, epigomisin O, epiwulignan A1 and tigloylgomisin P obtained from Example 3 were diluted with DMSO to a concentration of 200 mg/ml. These DMSO diluted solutions were diluted again with TPCK medium to a final concentration of 10 μg/ml and 50 μg/ml respectively to perform anti-viral activity tests. In addition, DMSO solutions were also serial diluted with TPCK medium to a final concentration of 100, 75, 50, 25, 12.5 and 6.25 μg/ml to determine its MIC of anti-viral activity.

Next, these compounds were applied and tested according to the following five test conditions: (1) cultivated MDCK cells (referring to EXAMPLE 2), harvested after removal of TPCK medium, were supplemented with 50 μl of above prepared compound solutions respectively and infected with 50 μl influenza virus H1N1 at 0.01 MOI at the same time. This group was designated as D+V group. (2) MDCK cells, collected after removal of TPCK medium, were treated with 50 μl of compound solutions respectively and 50 μl of TPCK medium. This group was designated D group. (3) MDCK cells, harvested after removal of TPCK medium, were infected with 50 μl influenza virus H1N1 at 0.01 MOI and supplemented with TPCK medium. This group was designated as V group. (4) MDCK cells, harvested after removal of TPCK medium, were supplemented with 100 μl TPCK medium. This group was designated as control group Mock. (5) The blank group contained neither MDCK cells nor TPCK medium. Moreover, anti-viral drug ribavirin (supplemented at concentration of 100~3.125 μg/ml) was used as the positive control group.

These test groups were incubated in incubator with controlled level of 5% $CO_2$ at 37° C. for 48 hrs. When the V group (the group treated with influenza virus alone) showed ≧75% of cell apoptosis under the microscope, MTT analysis was performed immediately. In the MTT test, the D+V group, D group, V group, the Mock control group, and the positive control group were supplemented with 20 μl of MTT (3-[4, 5-dimethylthiazol-2-yl]2,5-diphenyltetrazolium bromide) reagent (concentration at 5 mg/ml) and then allowed to react for 5 hours. In another set of test, the D+V group, D group, V group, the Mock control group, the positive control group, and the blank group were supplemented with 25 μl of glycine buffer and 100 μl of DMSO, followed by enzyme immunoanalysis at 540 nm. Cell survival ratio was calculated according to the following formulation:

$$\text{Cell survival ratio} = \frac{(D+V/D/V) - \text{Blank}}{\text{Mock}} \times 100\%$$

For cell survival ratio of ≦25%, >25% but ≦50%, >50% but ≦75%, >75% but ≦100%, or >100%, the results were recorded as +/−, +, ++, +++, or ++++, respectively. In which, the extracts that indicating effectiveness was defined as when (1) the cell survival ratio of the V group (the group that was treated with virus alone) must be less than 50% and (2) the extracts that could reverse cell apoptosis resulting from virus infection and the cell survival ratio must be higher than +++. The results were shown in Tables 9 and 10.

TABLE 9

Analysis anti-influenza virus activity of compounds purified from Schisandrae fructus

| | 50 μg/ml | | 10 μg/ml | |
|---|---|---|---|---|
| | D + V | D | D + V | D |
| Schisandrone | ++++ | ++++ | ++ | ++++ |
| Benzoylgomisin P | ++++ | +++ | +++ | +++ |
| Wulignan A1 | ++++ | ++++ | ++ | ++++ |
| Epigomisin O | ++++ | ++++ | ++ | ++++ |
| Epiwulignan A1 | ++++ | ++++ | + | ++++ |
| Tigloylgomisin P | +++ | +++ | +/− | ++++ |
| Ribavirin | +++ | ++++ | +++ | ++++ |

Table 9 showed that when 50 μg/ml of schisandrone, benzoylgomisin P, wulignan A1, epigomisin O, epiwulignan A1 and tigloylgomisin P were supplemented with the virus at the same time (the V+D group), cell survival ratio was 75~100% and more than 100%, suggesting that compounds isolated from Schisandrae fructus extracts had good anti-viral activity and could inhibit cell apoptosis resulting from influenza virus infection.

TABLE 10

MIC of various compounds purified from Schisandrae fructus

| | 100 μg/ml | | 75 μg/ml | | 50 μg/ml | | 25 μg/ml | | 12.5 μg/ml | | 6.25 μg/ml | |
|---|---|---|---|---|---|---|---|---|---|---|---|---|
| | D + V | D | D + V | D | D + V | D | D + V | D | D + V | D | D + V | D |
| Schisandrone | +/− | +/− | ++++ | ++++ | ++++ | ++++ | ++++ | ++++ | ++++ | ++++ | + | ++++ |
| Benzoylgomisin P | ++++ | ++++ | ++++ | ++++ | ++++ | +++ | ++++ | ++++ | +++ | ++++ | ++ | ++++ |
| Wulignan A1 | ++++ | ++++ | ++++ | ++++ | ++++ | ++++ | ++++ | ++++ | +++ | ++++ | ++ | ++++ |
| Epigomisin O | +/− | +/− | +/− | +++ | ++++ | ++++ | ++++ | ++++ | + | ++++ | + | ++++ |
| Epiwulignan A1 | ++++ | ++++ | ++++ | ++++ | ++++ | ++++ | +++ | ++++ | + | ++++ | + | ++++ |
| Tigloylgomisin P | ++++ | ++++ | ++++ | +++ | ++++ | +++ | + | ++++ | +/− | ++++ | +/− | ++++ |
| Ribavirin | +++ | ++++ | ++++ | +++ | ++++ | +++ | ++++ | ++++ | +++ | +++ | +++ | +++ |

The embodiment of the present invention further determined MIC and performed pharmaceutical toxicity of anti-viral compounds schisandrone, benzoylgomisin P, wulignan A1, epigomisin O, epiwulignan A1 and tigloylgomisin P. The results shown in Table 10 indicated that MIC of schisandrone, benzoylgomisin P and wulignan A1 was 12.5 μg/ml. MIC of epigomisin O and epiwulignan A1 was 25 μg/ml, while MIC of tigloylgomisin P was 50 μg/ml. Furthermore, pharmaceutical toxicity of benzoylgomisin P, wulignan A1, epiwulignan A1 and tigloylgomisin P was more than 100 μg/ml, while cytotoxicity of schisandrone and epigomisin O was 100 μg/ml and 75 μg/ml, respectively.

EXAMPLE 5

Anti-Influenza Virus Activity of the Extracts and Purified Compounds of Schisandrae fructus Against Drug Resistant Strain of H1N1-TR SCCH-EtOH and SCCH-H₂O prepared according to EXAMPLE 1 and schisandrone, benzoylgomisin P, wulignan A1, epigomisin O, epiwulignan A1 and tigloylgomisin P purified from the extract of Schisandrae fructus according to EXAMPLE 3, were analyzed their MIC of inhibitory activity against Tamiflu resistant H1N1-TR strain according to methods described in EXAMPLE 2 and EXAMPLE 4. The supplementation of ribavirin at concentration of 100~3.125 μg/mL was used as the positive control group.

TABLE 11

The anti-influenza virus activities of the extracts and purified compounds of Schisandrae fructus against H1N1 and H1N1-TR (a Tamiflu drug resistant virus strain)

| | MIC (μg/ml) | |
|---|---|---|
| | H1N1 | H1N1-TR* |
| SCCH-H$_2$O** | 200 | 50 |
| SCCH-EtOH*** | >200 | 50 |
| Schisandrone | 12.5 | 6.25 |
| Benzoylgomisin P | 12.5 | 12.5 |
| Wulignan A1 | 12.5 | 12.5 |
| Epigomisin O | 25.0 | — |
| Epiwulignan A1 | 25.0 | 12.5 |
| Tigloylgomisin P | 50.0 | 75.0 |
| Ribavirin | 3.125 | 3.125 |

*H1N1-TR was Tamiflu resistant virus strain
**SCCH-H$_2$O was crude extract of Schisandrae fructus obtained from 6 fold volume of distilled water extraction.
***SCCH-EtOH was crude extract of Schisandrae fructus obtained from 6-fold volume of ethanol extraction.

As shown in Table 11, MIC of schisandrone, benzoylgomisin P, and wulignan A1 was 12.5 μg/ml. MIC of epigomisin O and epiwulignan A1 was 25 μg/ml, while MIC of tigloylgomisin P was 50 μg/ml.

To summarize descriptions above, the methanol extract, the ethanol extract, and water extract of Schisandrae fructus and compounds of formula I, II, III, IV, V, and VI namely schisandrone, benzoylgomisin P, wulignan A1, epigomisin O, epiwulignan A1 and tigloylgomisin P, could inhibit influenza virus H1N1 activity. Thererfore, the methanol extract, the ethanol extract, and water extract of Schisandrae fructus and compounds of formula I, II, III, IV, V, and VI namely schisandrone, benzoylgomisin P, wulignan A1, epigomisin O, epiwulignan A1 and tigloylgomisin P could be applied in pharmaceutical composition in treatment of influenza virus H1N1 infection and inhibit the activity of influenza virus H1N1 or H1N1-TR (a Tamiflu drug resistant strain).

In addition to the effective amount of the compounds of formula I, II, III, IV, V, and VI, the pharmaceutical composition as described above could also contain pharmaceutically acceptable carriers. These carriers can be excipients (ex., water), filling agents (ex., sucrose or starch), bonding agents (ex., cellulose derivatives), diluents, disintegrating agents, or sweeteners, but not limited thereof. The pharmaceutical composition of the present invention can be prepared and produced according known methods, wherein effective amounts of active ingredients and one or more carriers are mixed in preparation of desired dosage form. The dosage form can be tablet, powder, pellet, capsule or other liquid form but not limited thereof.

What is claimed is:

1. A method of treating a H1N1 virus infection in a patient in need thereof consisting essentially of administering to said patient a therapeutically effective amount of a methanol/dichloromethane Schisandrae fructus extract.

* * * * *